US006934653B2

(12) United States Patent
Ritt

(10) Patent No.: US 6,934,653 B2
(45) Date of Patent: Aug. 23, 2005

(54) SYSTEM OR METHOD FOR CALIBRATING A RADIATION DETECTION MEDIUM

(75) Inventor: Daniel M. Ritt, Colorado Springs, CO (US)

(73) Assignee: Radiological Imaging Technology, Inc., Colorado Springs, CO (US)

( * ) Notice: Subject to any disclaimer, the term of this patent is extended or adjusted under 35 U.S.C. 154(b) by 44 days.

(21) Appl. No.: 10/445,587

(22) Filed: May 27, 2003

(65) Prior Publication Data

US 2003/0204336 A1 Oct. 30, 2003

Related U.S. Application Data

(63) Continuation of application No. 09/872,559, filed on Jun. 1, 2001, now Pat. No. 6,675,116.
(60) Provisional application No. 60/234,745, filed on Sep. 22, 2000, and provisional application No. 60/252,705, filed on Nov. 22, 2000.

(51) Int. Cl.[7] .................................................. G01F 1/00
(52) U.S. Cl. ..................................................... 702/104
(58) Field of Search .......................... 702/104, 49, 106, 702/114; 378/65, 98, 60; 382/132, 133, 128; 250/252, 374, 429, 322, 492.2, 492, 306, 370; 436/153; 600/3, 427, 410; 423/249; 430/322; 712/104; 324/557; 335/67

(56) References Cited

U.S. PATENT DOCUMENTS

| | | | |
|---|---|---|---|
| 5,095,217 A | | 3/1992 | Attix |
| 5,402,463 A | * | 3/1995 | Umetani et al. ........... 378/98.7 |
| 6,225,622 B1 | | 5/2001 | Navarro |
| 6,228,664 B1 | * | 5/2001 | Bronson et al. .............. 438/14 |
| 6,298,115 B1 | | 10/2001 | Nilsson |
| 6,333,964 B1 | * | 12/2001 | Hobel ....................... 378/98.7 |
| 6,345,114 B1 | | 2/2002 | Mackie et al. |
| 2001/0033678 A1 | * | 10/2001 | Hirai ........................... 382/128 |
| 2002/0106054 A1 | * | 8/2002 | Caflisch et al. ............... 378/65 |

OTHER PUBLICATIONS

Oldham et al.; "Improving Calibration Accuracy in Gel Dosimetry,"; Phys. Med. Biol., vol. 43 (1998), pp. 2709–2720.

Maryanski M. J. et al.; "Radiation Therapy Dosimetry Using Magnetic Resonance Imaging of Polymer Gels," Med. Phys. vol. 23, No. 5, May 1, 1996 pp. 699–705.

Oldham et al,. "An Investigation into the Dosimetry of a Nine–Field Tomotherapy Irradiation Using BANG–gel Dosimetry," Phys. Med. Biol., vol. 43 (1998), pp. 1113–1132.

(Continued)

Primary Examiner—Michael Nghiem
Assistant Examiner—Tung S. Lau
(74) Attorney, Agent, or Firm—Rader, Fishman & Grauer PLLC

(57) ABSTRACT

Methods and devices for calibrating a radiotherapy system are disclosed. The method includes providing a detection medium that responds to exposure to ionizing radiation, and preparing a calibration dose response pattern by exposing predefined regions of the detection medium to different ionizing radiation dose levels. The method also includes measuring responses of the detection medium in the predefined regions to generate a calibration that relates subsequent responses to ionizing radiation dose. Different dose levels are obtained by differentially shielding portions of the detection medium from the ionizing radiation using, for example, a multi-leaf collimator, a secondary collimator, or an attenuation block. Different dose levels can also be obtained by moving the detection medium between exposures. The disclosed device includes a software routine fixed on a computer-readable medium that is configured to generate a calibration that relates a response of a detection medium to ionizing radiation dose.

54 Claims, 6 Drawing Sheets

OTHER PUBLICATIONS

Kepka et al.; "A Solid–State Video film Dosimetry System," Phys. Med. Biol., vol 28, No. 4 (1983), pp. 421–426.

Yunping Zhu et al.; "Portal Dosimetry Using a Liquid Ion Chamber Matrix: Dose Response Studies,", Med. Phys., vol. 22, No. 7, Jul. 1995, pp. 1101–1106.

Munro P. et al.; "X–ray Quantum Limited Portal Imaging Using Amorphous Silicon Flat–Panel Arr;ays," Med. Phys., vol. 25, No. 5, May 1998, pp. 689–702.

J.M. Fitzpatrick, J.B. West, C.R. Manrer Jr., "Predicting Error in Rigid–Body Point Based Registration," IEEE Transactions on Medical Imaging, 17(5): 694–702, Oct. 1998.

ACR Bulletin "New Intensity–modulated Radiation Therapy Codes for Hospital Outpatient Procedures," Apr. 2001, vol. 57, Issue 4, pp. 4–5, 10.

* cited by examiner

SYSTEM OR METHOD FOR CALIBRATING A RADIATION DETECTION MEDIUM

RELATED APPLICATIONS

This continuation application claims the benefit of the following applications: utility application No. 09/872,559 (filed Jun. 1, 2001) now U.S. Pat. No. 6,675,116; provisional application No. 60/234,745 (filed Sep. 22, 2000); and provisional application No. 60/252,705 (filed Nov. 22, 2000).

BACKGROUND OF THE INVENTION

The present invention relates to radiation dosimetry, and more particularly to methods and devices for automating radiation dose calibrations associated with radiotherapy.

An important use of radiotherapy is the destruction of tumor cells. In the case of ionizing radiation, tumor destruction depends on the "absorbed dose" or the amount of energy deposited within a tissue mass. Radiation physicists normally express the absorbed dose in cGy units or centigray. One cGy equals 0.01 J/kg.

Radiation dosimetry generally describes methods to measure or predict the absorbed dose in various tissues of a patient undergoing radiotherapy. Accuracy in predicting and measuring absorbed dose is key to effective treatment and prevention of complications due to over or under exposure to radiation. Many methods exist for measuring and predicting absorbed dose, but most rely on developing a calibration—a curve or a lookup table—that relates the response of a detection medium to absorbed dose. Useful detection media include radiation-sensitive films and three-dimensional gels (e.g., 'BANG' and 'BANANA' gels) which darken or change color upon exposure to radiation. Other useful detection media include electronic portal-imaging devices and amorphous silicon detector arrays, which generate a signal in response to radiation exposure.

In order to develop a calibration curve or lookup table, discrete portions of the detection medium are exposed to different and known amounts of radiation using a linear accelerator or similar apparatus. Typically, about twelve, but often as many as twenty-five different radiation dose levels are measured in order to generate a calibration curve or look-up table. Generally, the accuracy of the calibration increases as the number of measured radiation dose levels increases. However, measuring separate radiation dose levels is a labor intensive and time consuming process, which can be demonstrated by examining a calibration process for radiation film dosimetry.

As shown in FIG. 1A and FIG. 1B, a linear accelerator 100 is used to expose different areas of a radiographic calibration film 102 to ionizing radiation 104. The film 102 is typically sandwiched between layers 106 of material that mimic the response of human tissue to the ionizing radiation 104. A shield 108, which is made of a dense material such as lead, is interposed between the film 102 and the linear accelerator 100. The shield 108 has a fixed aperture 110, which only permits ionizing radiation 104 to reach an area of the film 102 that is aligned with the aperture 110. During calibration, the area of the film 102 that is aligned with the aperture 110 is exposed to a known and unique dose of ionizing radiation 104, while other areas of the film 102 are masked by the shield 108. The absorbed dose can be obtained from ion chamber measurements, Fricke dosimetry, calorimetry, or other absolute dosimetry methods. Because of the high radiation levels involved, the physicist must leave the room and close shielding doors during each exposure of the film 102. After exposing the film 102 to radiation, the physicist reenters the room and moves the film 102 to align a previously unexposed area of the film 102 with the aperture 110. The physicist then leaves the room, secures the shielding doors, and sets the linear accelerator 100 controls to deliver the next dose level. This process is repeated for each dose level in the calibration sequence.

FIG. 2 shows three radiographic calibration films 102 that have been exposed to different radiation dose levels during a calibration sequence. Each of the films 102 have discrete areas 120 that have been exposed to different radiation dose levels, which range from 0 cGy to 220 cGy. Normally, the radiation dose levels of the calibration films 102 are obtained throughout a range of dose levels that are expected during radiation therapy, and generally range from 0 cGy to as much as 6,000 cGy. The step sizes between successive calibration dose levels can vary and depend on the dynamic range of the detection medium used. Ordinarily, the calibration films 102 are scanned with a film digitizer, which converts each of the films to an array of pixels having values representing the optical density at each point on a particular calibration film 102.

FIG. 3 shows a sample calibration or H&D curve 140 obtained from the calibration films 102 shown in FIG. 2. Usually, specialized software averages the optical density over the discrete areas 120 of the calibration films 102, and generates a calibration curve or look-up table based on known values of the radiation dose levels and the measured optical density. Armed with the H&D curve 140 (or other calibration), the radiation physicist can quantify beam characteristics of the linear accelerator through subsequent exposure, development, and optical density measurements of radiographic films. For example, as part of a treatment plan or quality assurance procedure, the radiation physicist can use film dosimetry to generate depth dose profiles, isodose and isodensity contours, and cross section profiles. In addition, the physicist can use film dosimetry to perform flatness and symmetry analyses, and to carry out field width calculations, among others. Usually, the physicist uses computer software that automatically calculates and displays beam characteristics from scanned and digitized radiographic films. Useful software for generating the H&D curve and for analyzing radiotherapy beam characteristics includes RIT113 FILM DOSIMETRY SYSTEM, which is available from Radiological Imaging Technology.

Calibration procedures, such as the method described above for film dosimetry, have several disadvantages. First, regardless of the detection media used, the methods require a large number of labor- and time-intensive steps to expose the requisite dose levels needed to generate the calibration. Second, care must be taken to ensure that in each calibration step a previously unexposed area of the detection media is used. If the dose areas overlap, the calibration data can be meaningless. Third, because of the relatively large number of films that must be exposed in film dosimetry, short-term drift in radiation response from one film to the next can occur because of changes in film processor chemistry and temperature.

The present invention overcomes, or at least mitigates, one or more of the problems described above.

SUMMARY OF THE INVENTION

One aspect of the invention provides a method for calibrating a radiotherapy system. The method includes providing a detection medium, such as radiographic film, which is adapted to respond to exposure to ionizing radiation. The method also includes preparing a calibration dose response pattern by exposing predefined regions of the detection medium to different ionizing radiation dose levels, and measuring responses of the detection medium in the predefined regions. The different dose levels are obtained by differentially shielding portions of the detection medium from the ionizing radiation using, for example, a multi-leaf collimator, a secondary collimator, or an attenuation block. Usually, the ionizing radiation characteristics (e.g., beam intensity, duration of exposure, etc.) are also changed between individual exposures of the detection medium, causing the delivered dose to vary among different predefined regions. The different dose levels can also be obtained by moving the detection medium relative to the source of ionizing radiation between exposures, while changing the ionizing radiation characteristics from one exposure to the next. From the measured responses, the method generates a calibration curve or look-up table that relates the subsequent response of the detection medium to ionizing radiation dose.

Another aspect of the invention provides a device for calibrating a radiotherapy system. The device includes a software routine tangibly embodied or fixed on a computer-readable medium. The software routine is configured to generate a calibration that relates a response of a detection medium to ionizing radiation dose. In accordance with the invention, the software routine generates the calibration from a dose response pattern having predefined regions exposed to different ionizing radiation dose levels. The different dose levels are obtained by differentially shielding portions of the detection medium from the ionizing radiation or by moving the detection medium relative to the source of ionizing radiation between exposures, while changing the ionizing radiation characteristics from one exposure to the next. Generally, the software routine runs on a computer having a graphical user interface, which allows interaction between the software routine and the user.

The invention offers significant advantages over conventional, labor-intensive calibration procedures. Because the invention automates the calibration process, it significantly reduces the amount of time necessary to expose a detection medium to different dose levels during a calibration sequence. Additionally, because the dose response pattern of the detection medium is highly repeatable and known, computer software algorithms can be used to automatically measure the radiation dose response and to automatically generate the calibration curve or look-up table. Finally, by significantly reducing the number of calibration films or other detection media needed to generate a calibration, the claimed process has much higher short-term stability. All of these advantages should result in better accuracy in radiation dosimetry and improved patient care.

DETAILED DESCRIPTION

The present invention generally comprises automatically exposing predefined areas or regions of a detection medium to known radiation dose levels, and measuring the response of the detection medium to the radiation dose levels. Knowing the response of the detection medium to different values of the dose level, one can generate a calibration curve or look-up table. The calibration, which relates the response of the detection medium to radiation exposure, can then be used to convert subsequent radiation exposure and response to absorbed dose.

As described below, various techniques and devices can be used to automatically expose predefined regions of the detection medium to different dose levels. One method employs multi-leaf collimators, secondary collimators or fixed blocks of radiation attenuating material, either alone or in combination, to differentially shield the predefined regions during exposure to ionizing radiation. The ionizing radiation characteristics (e.g., beam intensity, individual exposure duration, etc.) can remain unchanged between each exposure, and the delivered dose will vary among different predefined regions because the detection medium is differentially shielded during each exposure. Optionally, the beam characteristics can vary between one or more of the exposures. A second method uses a moveable patient couch or similar apparatus to move the detection medium relative to the ionizing radiation beam, and delivered dose is varied between different predefined regions of the detection medium by changing the ionizing radiation characteristics between exposures.

Figure 4:
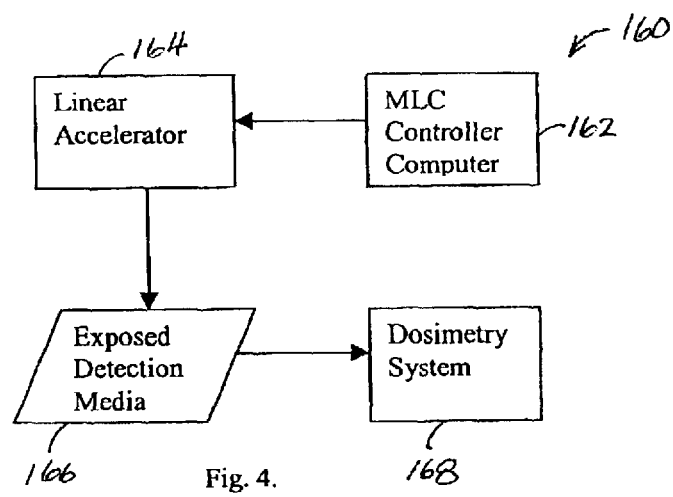
FIG. 4 shows a block diagram of an automatic calibration process and system for radiation dosimetry.
Figure 5A:
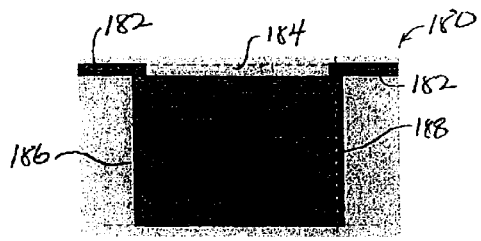
FIG. 5A through FIG. 5M show multi-leaf collimator (MLC) patterns with 2, 4, 6, 8, 10, 12, 14, 16, 18, 20, 22, 24 and 26 leaves open on both sides, respectively.
Figure 5B:
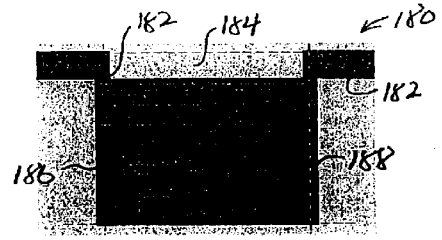
Figure 5C:
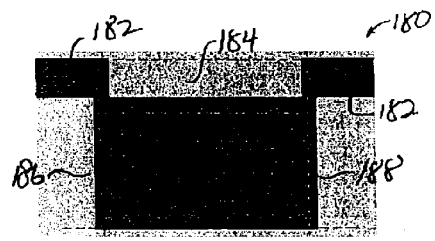
Figure 5D:
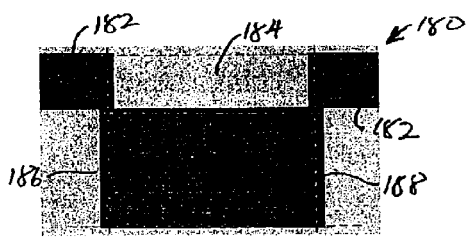
Figure 5E:
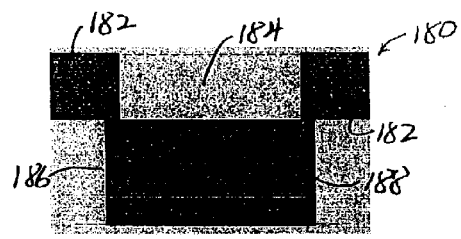
Figure 5F:
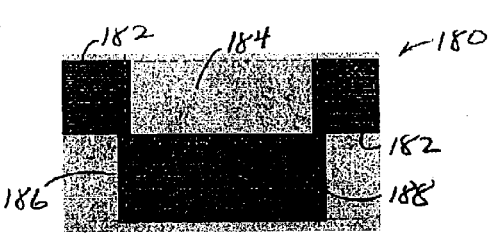
Figure 5G:
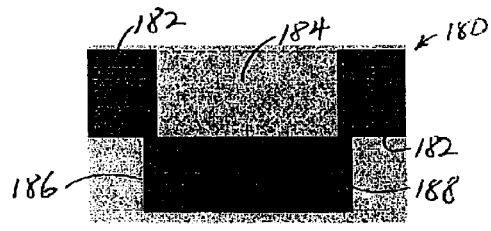
Figure 5H:
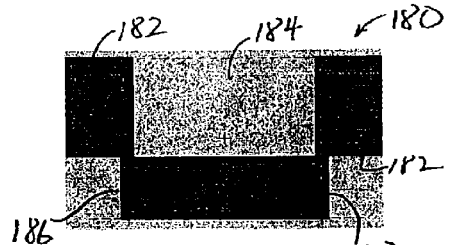
Figure 5I:
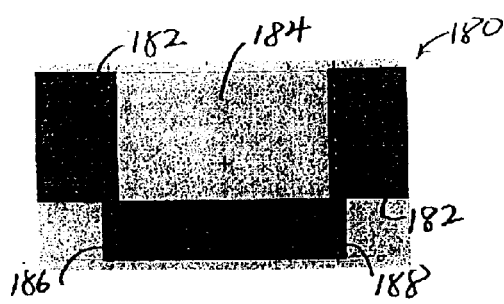
Figure 5J:
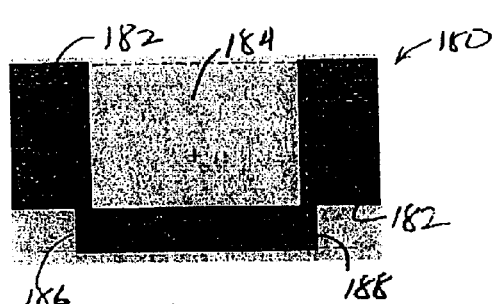
Figure 5K:
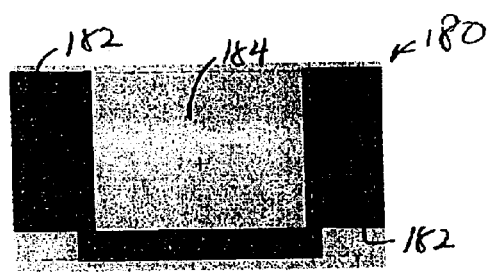
Figure 5L:
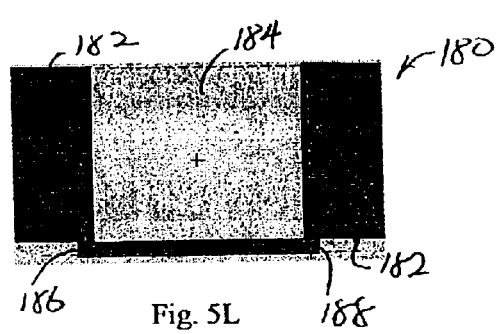
Figure 5M:
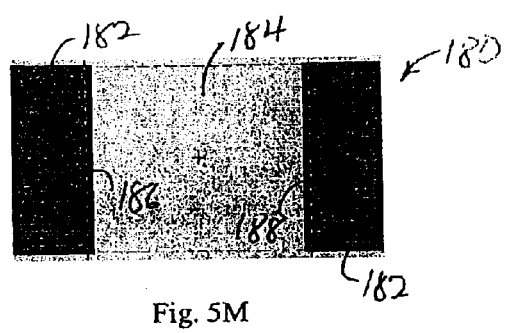

FIG. 4 shows a block diagram of one embodiment of an automatic calibration process and system 160 for radiation dosimetry. The calibration system 160 shown in FIG. 4 uses a multi-leaf collimator (MLC) to automatically expose predefined areas or regions of a detection medium to different and known radiation dose levels. Newer linear accelerators use multi-leaf collimators for shaping the dose beam during radiotherapy. A multi-leaf collimator comprises interleaved collimators made of lead (or other high-density material) that move independently in or out of the radiation field to shape the beam. Compared with some lead blocks, multi-leaf collimators allow the radiation physicist to more closely tailor the shape of the beam to match the area of the body undergoing treatment. Further details concerning multi-leaf collimators and shielding blocks can be found in Peter Metcalfe et al., *The Physics of Radiotherapy X-Rays from Linear Accelerators* 31–32, 268–72 (1997), which is herein incorporated by reference.

As shown in FIG. 4, the system calibration 160 includes a MLC controller computer 162 and a linear accelerator 164 having a multi-leaf collimator. During a calibration sequence, the MLC controller 162 provides instructions to a linear accelerator 164 for regulating radiation beam characteristics and for adjusting positions of individual leaves of the multi-leaf collimator. Through appropriate positioning of the leaves, the calibration system 160 automatically (i.e., with minimal human intervention) exposes predefined areas or regions of a detection medium 166 to known radiation dose levels, which results in a radiation dose response pattern on the detection medium 166. The detection medium 166 can be any material or device that will respond in a consistent way to radiation exposure, and includes radiographic film, 3-D BANG or BANANA gels, amorphous silicon arrays, electron portal imaging devices, and the like. A dosimetry system 168 measures the response of the detection medium 166 in each of the predefined areas of the detection medium 166 and generates a calibration curve or look-up table. For film dosimetry, the system 168 would likely include a film scanner for digitizing calibration films, and software running on a computer for generating the calibration curve or look-up table and for performing dosimetry calculations. Following subsequent exposure of the detection medium—i.e., unexposed test films or gels, amorphous silicon array, and so on—the calibration curve or look-up table can be used to convert the radiation dose response of the detection medium to absorbed dose.

FIG. 5A through FIG. 5M show sample leaf positions of a multi-leaf collimator (MLC) 180 during a calibration sequence. The multi-leaf collimator 180 is comprised of interleaved collimators or leaves 182 that move independently in or out of the radiation field 184 from the sides 186, 188 of the MLC 180. FIG. 5A through FIG. 5M show MLC 180 patterns with 2, 4, 6, 8, 10, 12, 14, 16, 18, 20, 22, 24 and 26 leaves 182 open on both sides 186, 188 of the MLC 180. As noted above, movements of the leaves 182 in FIG. 5A through FIG. 5M, as well as the characteristics of the radiation beam (intensity, duration, etc.), are coordinated by an MLC controller computer based on input by the operator. Accordingly, the amount of radiation exposure on various predefined areas or regions of the detector medium are known or can be obtained by absolute dosimetry (e.g., ionization chamber measurements).

Figure 2:
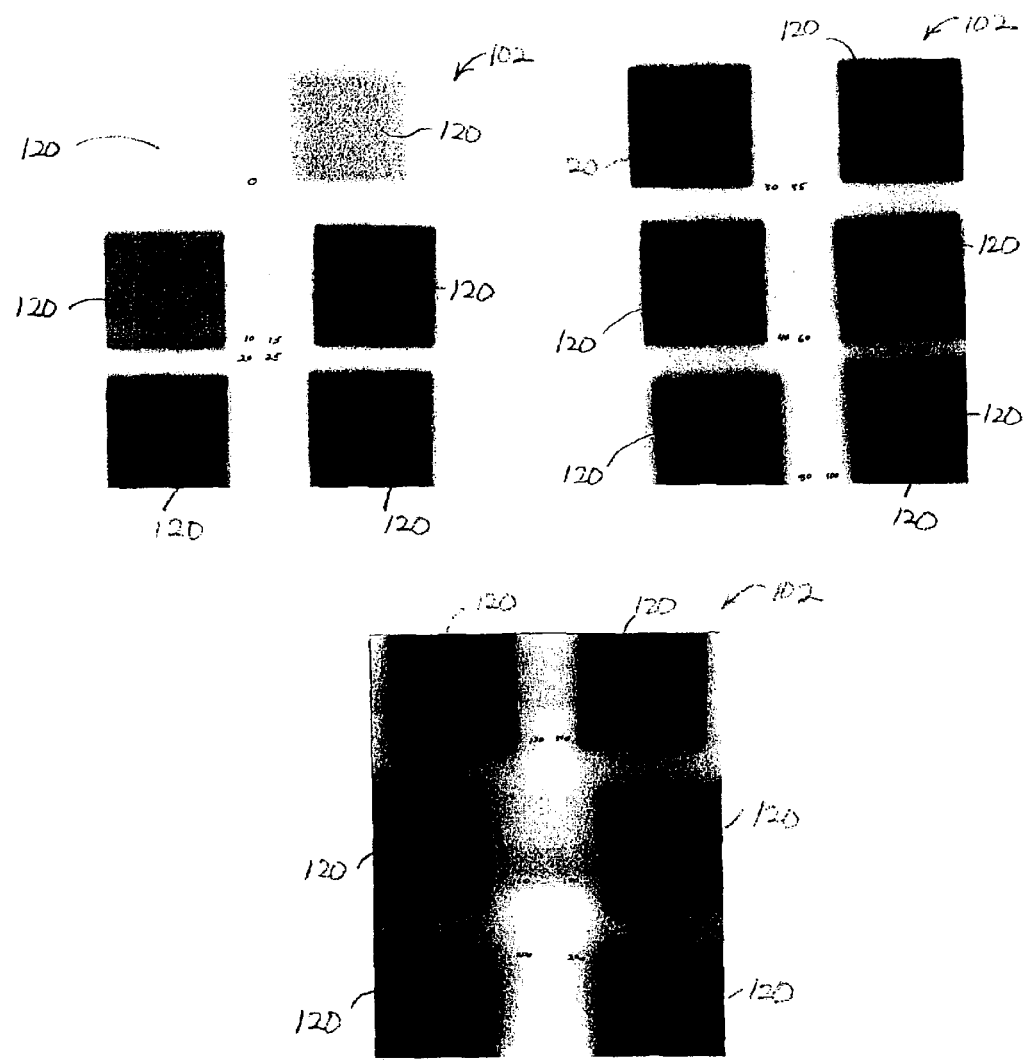
FIG. 2 shows three radiographic films that have been exposed to different radiation dose levels during a calibration sequence.
Figure 3:
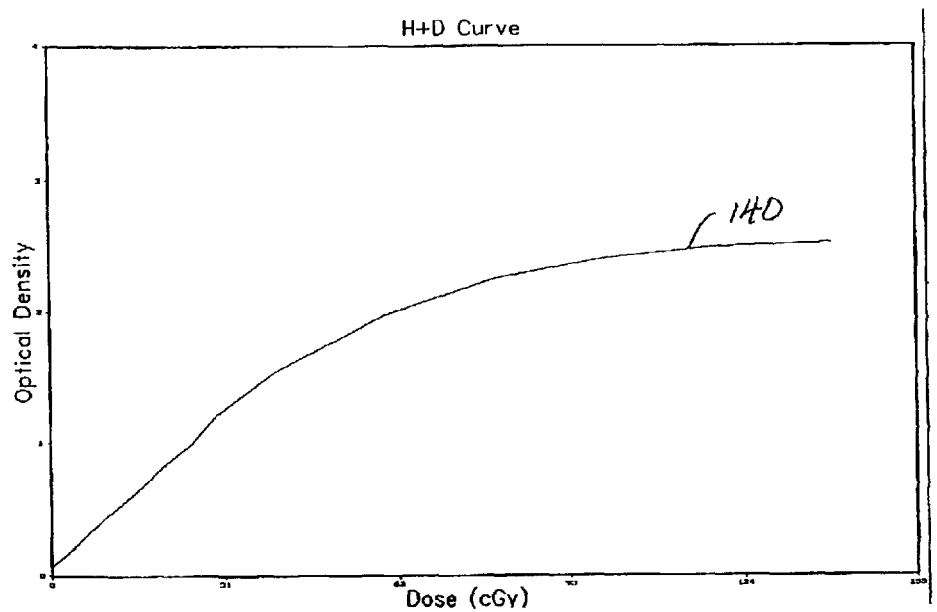
FIG. 3 shows a calibration curve (H&D curve), which can be used to convert optical density of radiographic film to absorbed dose.

Individual leaves 182 of the multi-leaf collimator 180 respond quickly to instructions from the MLC controller 162—usually within less than about five seconds, and often less than about one second. Individual radiation exposures depend on the dose delivery rate of the radiation source, the dose response of the detection medium, and the dose level expected during radiation therapy. Because commercially available linear accelerators can typically deliver about 600 cGy per minute, and most radiotherapies require dose levels less than about 1000 cGy, individual radiation exposures are typically on the order of a few seconds to a few minutes. Therefore, a twelve-step calibration exposure sequence on a single film or detection medium ordinarily can be completed in less than about five minutes, and usually in less than about two minutes. In some cases, the exposure sequence can be completed in less than about one minute. In any event, the entire calibration exposure sequence can be completed in much less than time than conventional processes. For example, an operator could generally complete a twelve-step manual calibration exposure sequence, similar to the one illustrated in FIG. 2, in about forty-five minutes.

Figure 6:
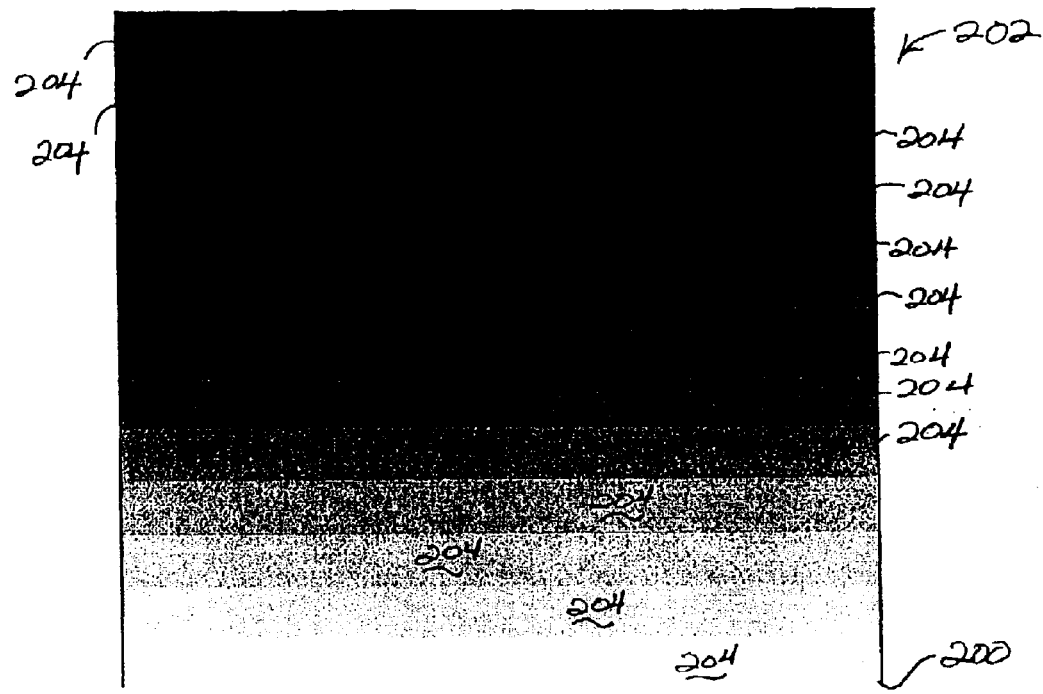
FIG. 6 shows the resulting film exposure after executing the multi-leaf collimator patterns in FIG. 5A through FIG. 5M.

FIG. 6 shows a calibration film 200 having a radiation dose response pattern 202 corresponding to the MLC 180 leaf 182 positions of FIG. 5A through FIG. 5M. The calibration film 200 is scanned with a film digitizer, which converts the dose response pattern 202 to an array of pixels having values representing the optical density at each point on the calibration film 200. Because the dose response pattern 202 is known, dosimetry software can be used to automatically average the optical density over each of the predefined areas 204 or regions of the calibration film 200 (pixel array) and to generate a calibration curve or look-up table. Ordinarily the dosimetry software routine should measure the dose response away from edges 206 of the predefined areas 204 because radiation leakage between the leaves 182 could result in artificially high dose levels.

Dose response patterns besides the step-gradient pattern 202 shown in FIG. 6 can be generated through appropriate programming of the MLC controller computer 162 of FIG. 4. For example, the step-gradient dose response pattern 202 of FIG. 6 was obtained through multiple exposures of the predefined areas 204 of the calibration film 200. The beam characteristics were not changed between successive exposures of the film 200, and differences in optical density among the predefined areas 204 of the film 200 resulted from differences in the number of radiation exposures. Other patterns can be obtained by changing the beam characteristics between successive exposures. For example, the MLC (or other shielding device) can be used to completely mask areas of the detector medium so that the dose response pattern resembles FIG. 2. In such cases, the beam characteristics—duration, intensity, etc.—are changed in a predetermined way to effect different radiation dose responses of the detector medium. Similarly, the beam characteristics could have been changed between successive exposures of the calibration film 200 shown in FIG. 6.

Figure 7:
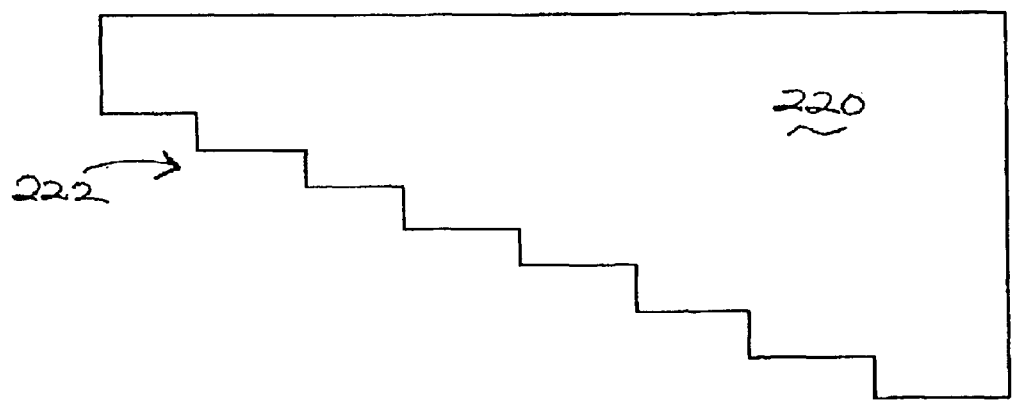
FIG. 7 shows a radiation attenuation block for generating radiation dose response patterns for radiotherapy calibrations.

Other embodiments can include the use of fixed blocks and secondary collimators ("jaws") to automatically expose predefined areas or regions of the detection medium to known radiation dose levels. For example, older linear accelerators and other types of radiation generating devices (such as Co-60 sources) can use a fixed block of ionizing radiation attenuating material to create predefined exposure areas. FIG. 7 shows one such block 220 having a step pattern 222 that would mimic the multi-leaf collimator 180 patterns and dose response pattern 202 shown in FIG. 5A through FIG. 5M and FIG. 6, respectively. In addition, the secondary collimators of a linear accelerator can be used to achieve a similar dose response pattern. Secondary collimators are large radiation attenuators typically made of lead alloy or tungsten, and can undergo precise movement. On most linear accelerators, the secondary collimators can be programmed to move to specific locations in order to attenuate the radiation exposure, and can therefore be adapted to simulate the radiation response pattern 202 of FIG. 6 and others. Whether using fixed blocks or secondary collimators, measurements of the radiation dose response should ordinarily be carried out in areas of uniform dose exposure, away from any transition regions between the predefined exposure areas on the detection medium. Further details concerning secondary collimators can be found in Metcalfe et al. at 28–29, which is herein incorporated by reference.

Figure 1A:
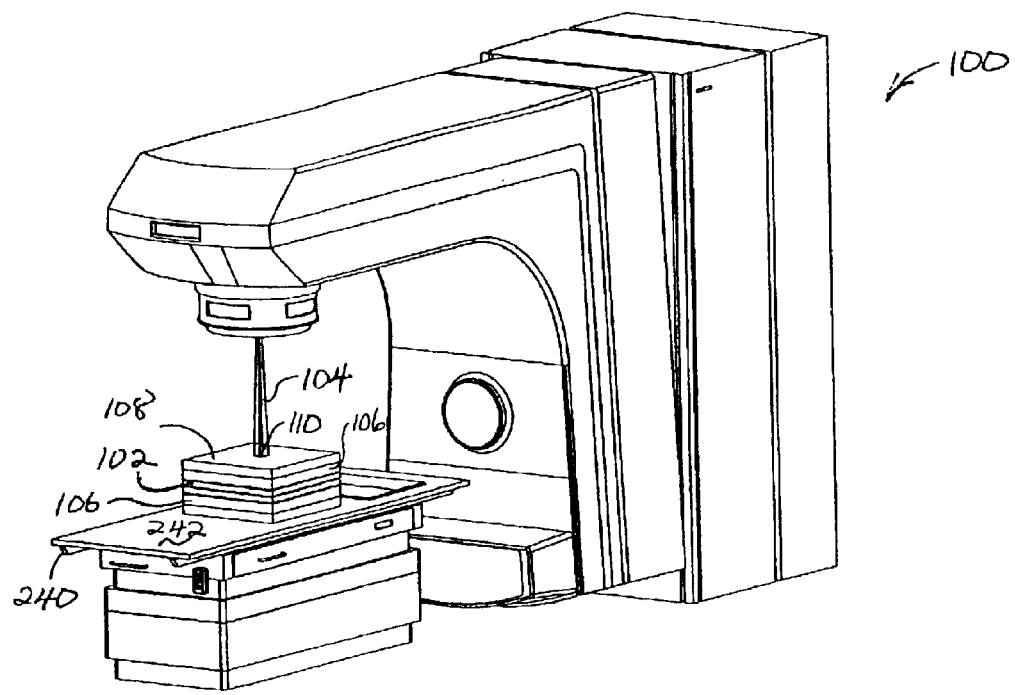
FIG. 1A and FIG. 1B show a linear accelerator used to expose different areas of a radiographic film to ionizing radiation.
Figure 1B:
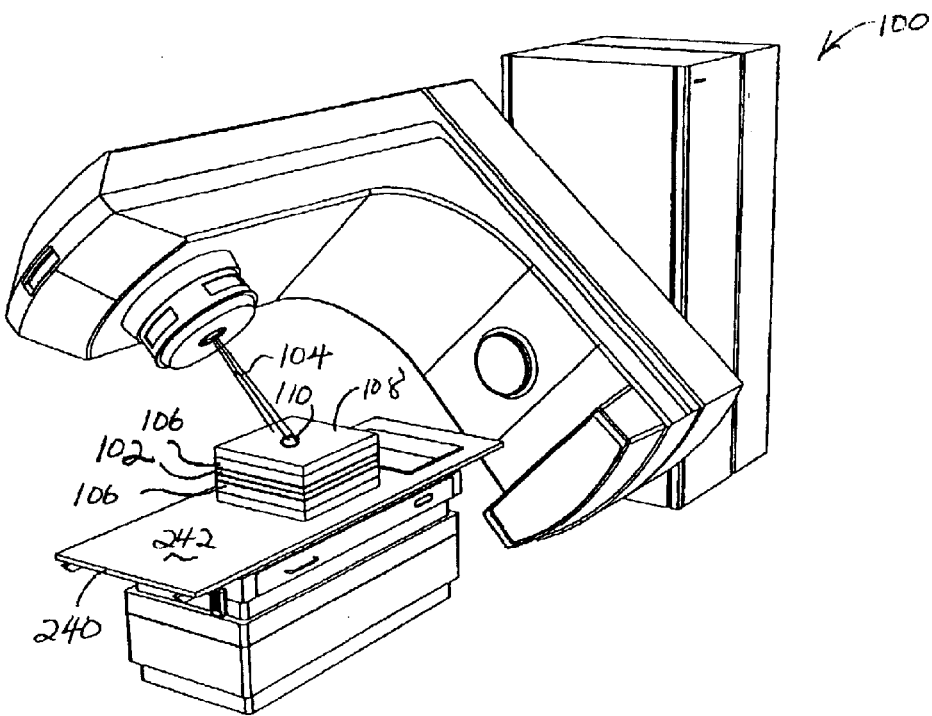

Instead of or in addition to regulating the beam exposure pattern by differentially shielding the predefined regions of the detection medium, one may automatically expose predefined areas or regions of the detection medium to known radiation dose levels by moving the detection medium between exposures. Referring to FIG. 1, the detection medium (e.g., radiographic calibration film 102) can be placed on a surface 240 of a patient couch 242, which is capable of precise, three-dimensional motion, including translation and rotation in a plane containing the surface 240 of the couch 242, and movement perpendicular to the plane containing the surface 240. During a calibration sequence, a controller (not shown) provides instructions to the linear accelerator 100 for regulating radiation beam 104 characteristics (beam 104 intensity and duration) and for adjusting the position of the patient couch 242 and detection medium relative to the ionizing radiation beam 104. The patient couch 242 can respond quickly to the controller. Depending on the distanced moved, the patient couch 242 can usually respond within less than about one minute, and usually less than about five seconds. Therefore, an entire calibration exposure sequence obtained by moving the detection medium relative to the source of ionizing radiation can be completed in about the same amount of time as using a multi-leaf collimator, secondary collimator, or attenuation block to regulate the beam exposure pattern.

Thus, one may obtain a dose response pattern similar to the step-gradient 202 shown in FIG. 6 by first adjusting the secondary collimator, the multi-leaf collimator, or the secondary and multi-leaf collimators, to expose a rectangular region of the detection medium corresponding to one of the predefined areas 204. Following exposure to ionizing radiation 104, the controller moves the patient couch 242 and the detection medium, and directs the linear accelerator 104 to expose another predefined area 204 to a different dose. This process is continued until the requisite number of dose levels is obtained.

One may employ other devices for moving the detection medium relative to the beam 104, such as a computer-controlled x-y coordinate stage that is adapted to displace the detection medium in about one-half mm increments or about 0.1-degree arcs. As should be appreciated, one may obtain dose response patterns different than the step-gradient 202 shown in FIG. 6 by adjusting the shape of the ionizing radiation beam 104 prior to the first exposure, and optionally, between successive exposures of the predefined regions of the detection medium. The shape of the beam 104 conforms to the shape of the predefined region or regions during a particular exposure.

When compared to calibration routines involving multi-leaf collimators, the use of a moving detection medium may provide more accurate delivered dose. Using a secondary collimator instead of a multi-leaf collimator to shape the beam should result in more uniform radiation exposure in each of the predefined regions of the detection medium. As indicated in the discussion of FIG. 5A through FIG. 5M, radiation leakage between the leaves 182 of a multi-leaf collimator 180 may result in artificially high dose levels near the edges 206 of the predefined areas 204 shown in FIG. 6.

In any event, the disclosed automatic calibration processes and systems for radiation dosimetry provide significant advantages over conventional methods and devices. As noted above, the disclosed processes can complete a calibration exposure sequence in much less time and with much less operator intervention than conventional labor-intensive calibration methods. In addition, as described in the background section, conventional dose response patterns on film depend on the manual placement of the film, resulting in an arbitrary spatial distribution. Consequently, in conventional calibration exposure processes the dosimetry software user must specify the location of each area of the film (pixel array) that corresponds to a specific dose level.

Although it may be possible to develop computer software algorithms that can automatically locate the different exposure regions in conventionally exposed films, such routines will be comparatively much more difficult to implement because the dose response pattern is unknown and varies from film to film. Unlike conventional calibration techniques and devices, the use of a MLC or similar attenuating device allows one to obtain dose response data using a single calibration film or detection medium because of the precise spatial arrangement of the dose response pattern. Thus, for example, the automated calibration methods and devices allow one to obtain dose response patterns having ten, twenty, thirty, forty, and fifty or more different dose levels on a single detection medium such as a radiographic film.

As noted above, radiation physicists typically use computer software that automatically calculates and displays calibration curves, look-up tables, and beam characteristics from the dose response patterns. Software routines generally control positions of primary, secondary, and multi-leaf collimators, and also adjust the position of the patient couch. Thus, portions of the disclosed calibration methodology are typically implemented as software routines that run on a processor. Suitable processors include, for example, both general and special purpose microprocessors. Typically, the processor receives instructions and data from a read-only memory and/or a random access memory. Computer instructions and data are loaded into the read-only memory and/or the random access memory from a storage device or computer readable medium. Storage devices suitable for tangibly embodying computer program instructions and data include all forms of non-volatile memory, including, for example, semiconductor memory devices, such as EPROM, EEPROM, and flash memory devices; magnetic disks such as internal hard disks and removable disks; magneto-optical disks; and CD-ROM, CD-R and CD-RW disks. One may supplement any of the foregoing by, or incorporate in, ASICs (application-specific integrated circuits).

To provide interaction with a user, one can implement portions of the calibration methods on a computer system having devices for displaying information to the user and for allowing the user to input information to the computer system. Useful display devices include a monitor and LCD screen; suitable input devices include a keyboard, which can be used with a pointing device such as a pressure-sensitive stylus, a touch pad, a mouse or a trackball. In addition, the computer system may provide a graphical user interface through which the computer routines interact with the user.

The above description is intended to be illustrative and not restrictive. Many embodiments and many applications besides the examples provided would be apparent to those of skill in the art upon reading the above description. The scope of the invention should therefore be determined, not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method for calibrating a sequence of doses, comprising:
    identifying a number of doses in the sequence of doses;
    dividing a detection medium into a plurality of predefined regions;
    selecting a dose level for each predefined region on the detection medium;
    exposing each predefined region on the detection medium with the selected dose of radiation;
    measuring a plurality of responses in the detection medium; and
    calculating a calibration from the plurality of responses.

2. The method of claim 1, wherein each predefined region of the detection medium is exposed with the selected dose of radiation without human intervention between exposures.

3. The method of claim 1, wherein the calibration is not calculated with respect to a particular patient.

4. The method of claim 1, wherein the calibration is usable with respect to the treatment of multiple patients.

5. The method of claim 1, wherein no human intervention occurs between the first and last measuring of responses in the detection medium.

6. The method of claim 1, wherein a sequence of at least twelve responses are measured and incorporated into a single calibration in less than approximately five minutes.

7. The method of clam 1, wherein the calibration represents a relationship between a dose and the detection medium.

8. The method of claim 1, wherein the calibration does not represent a relationship between a dose and a particular patient.

9. The method of claim 1, wherein exposing each predefined region on the detection medium with the selected dose of radiation without human intervention between exposures includes at least one of: (a) moving the detection medium relative to a linear accelerator; and (b) shielding the detection medium.

10. The method of claim 9, wherein exposing each predefined region on the detection medium with the selected dose of radiation without human intervention between exposures includes moving the detection medium relative to a linear accelerator and shielding the detection medium.

11. The method of claim 1, wherein each predefined region is exposed to a different dose level.

12. The method of claim 1, wherein the detection medium is sandwiched between layers of material that mimic a response of human tissue to ionizing radiation.

13. The method of claim 1, wherein the detection medium is a three dimensional gel.

14. The method of claim 1, wherein measuring occurs at a distance from the edge of the predefined areas that is no smaller than a predefined minimum distance.

15. The method of claim 1, wherein no predefined area is subjected to more than one dose of radiation.

16. The method of claim 1, wherein a correction factor is not used to calculate the calibration.

17. The method of claim 1, wherein a graphical user interface provides for accepting as inputs, the number of doses and a sequence of dose levels.

18. A calibration system for a radiotherapy application, comprising:
  a detection medium, said detection medium including a plurality of predefined regions, wherein said detection medium provides for the absorption of a plurality of doses;
  a linear accelerator, said linear accelerator configured to expose said plurality of predefined regions to said plurality of doses, said plurality of doses including a plurality of dose levels, with each said dose being of one said dose level;
  a plurality of measured responses resulting from the exposure of said detection medium to said plurality of individual doses; and
  a calibration generated from said plurality of measured responses on said detection medium.

19. The system of claim 18, wherein the number of doses is equal to the number of predefined regions, and wherein each predefined region is exposed to only one dose.

20. The system of claim 19, wherein said dose level is different for each said predefined region.

21. The system of claim 18, wherein said detection medium is exposed to said plurality of doses in a sequence of doses, and wherein said plurality of predefined regions are exposed one at a time within said sequence.

22. The system of claim 21, wherein no human intervention occurs during said sequence.

23. The system of claim 18, wherein said plurality of measured responses are analyzed in a sequence of measurements, and wherein said plurality of measured responses are analyzed individually within said sequence.

24. The system of claim 23, wherein no human intervention occurs during said sequence.

25. The system of claim 18, wherein said calibration is not specific to a particular patient.

26. The system of claim 18, wherein said calibration is calculated from a sequence of at least six doses, and wherein an elapsed time for calculating said calibration from said detection medium is less than approximately ten minutes.

27. The system of claim 18, wherein said calibration represents a relationship between said linear accelerator and said detection medium.

28. The system of claim 18, wherein said plurality of measured responses are displayed in the form of a step-gradient pattern.

29. A calibration system for a radiotherapy application comprising:
  a detection medium adapted to respond to exposure to ionizing radiation, said detection medium including a plurality of predefined regions wherein said detection medium is sandwiched between layers of material that mimic a response of human tissue to ionizing radiation;
  a computer, including a graphical user interface providing for the input and output of data, wherein said input data includes a number of predefined regions, a number of doses, a sequence of dose levels, and a plurality of configuration attributes, wherein said configuration attributes relate to the automated exposure of said detection medium to ionizing radiation;
  a means for irradiating predefined regions of the detection medium with different ionizing radiation dose levels in accordance with said input data; and
  a dosimetry application configured to automatically measure responses of the detection medium in the predefined regions and automatically relate a response of the detection medium to an ionizing dose level, said dosimetry application generating a calibration from said responses in the form of said output data.

30. The system of claim 29, further comprising a beam of ionizing radiation shaped in accordance with said input data so that the beam substantially conforms to the predefined region or regions being exposed.

31. The system of claim 30, further comprising a multi-leaf collimator used to shape said beam of ionizing radiation.

32. The system of claim 30, further comprising a secondary collimator used to shape said beam of ionizing radiation.

33. The system of claim 29, further comprising an automated shield mechanism positioned in accordance with said input data, wherein said automated shield mechanism differentially shields portions of the detection medium from ionizing radiation.

34. The system of claim 33, wherein said automated shield mechanism is a multi-leaf collimator used to differentially shield said beam of ionizing radiation.

35. The system of claim 33, further comprising a secondary collimator used to differentially shield said beam of ionizing radiation.

36. The system of claim 33, further comprising a fixed block having ionizing radiation attenuation characteristics that vary across a surface of the fixed block for differentially shielding the beam of ionizing radiation.

37. The system of claim 29, wherein the means for irradiating predefined regions of the detection medium with different ionizing radiation dose levels includes adjusting the characteristics of the beam of ionizing radiation in accordance with said input data.

38. A computer readable medium comprising instructions executable by a computer for calibrating a sequence of doses, said instructions configured to instruct the computer to perform steps comprising:

identifying a number of doses in the sequence of doses;

dividing a detection medium into a plurality of predefined regions;

selecting a dose level for each predefined region on the detection medium;

exposing each predefined region on the detection medium with a selected dose of radiation corresponding to the selected dose level;

measuring a plurality of responses in the detection medium; and calculating a calibration from the plurality of responses.

39. The computer readable medium of claim 38, wherein each predefined region of the detection medium is exposed with the selected dose of radiation without human intervention between exposures.

40. The computer readable medium of claim 38, wherein the calibration is not calculated with respect to a particular patient.

41. The computer readable medium of claim 38, wherein the calibration is usable with respect to the treatment of multiple patients.

42. The computer readable medium of claim 38, wherein no human intervention occurs between the first and last measuring of responses in the detection medium.

43. The computer readable medium of claim 38, wherein a sequence of at least twelve responses are measured and incorporated into a single calibration in less than approximately five minutes.

44. The computer readable medium of claim 38, wherein the calibration represents a relationship between a dose and the detection medium.

45. The computer readable medium of claim 38, wherein the calibration does not represent a relationship between a dose and a particular patient.

46. The computer readable medium of claim 38, wherein exposing each predefined region on the detection medium with the selected dose of radiation without human intervention between exposures includes at least one of: (a) moving the detection medium relative to a linear accelerator; and (b) shielding the detection medium.

47. The computer readable medium of claim 46, wherein exposing each predefined region on the detection medium with the selected dose of radiation without human intervention between exposures includes moving the detection medium relative to a linear accelerator and shielding the detection medium.

48. The computer readable medium of claim 38, wherein each predefined region is exposed to a different dose level.

49. The computer readable medium of claim 38, wherein the detection medium is sandwiched between layers of material that mimic a response of human tissue to ionizing radiation.

50. The computer readable medium of claim 38, wherein the detection medium is a three dimensional gel.

51. The computer readable medium of claim 38, wherein measuring occurs at a distance from the edge of the predefined areas that is no smaller than a predefined minimum distance.

52. The computer readable medium of claim 38, wherein no predefined area is subjected to more than one dose of radiation.

53. The computer readable medium of claim 38, wherein a correction factor is not used to calculate the calibration.

54. The computer readable medium of claim 38, wherein a graphical user interface provides for accepting as inputs, the number of individual doses and a sequence of dose levels.

* * * * *

UNITED STATES PATENT AND TRADEMARK OFFICE
CERTIFICATE OF CORRECTION

PATENT NO. : 6,934,653 B2
DATED : August 23, 2005
INVENTOR(S) : Daniel M. Ritt

It is certified that error appears in the above-identified patent and that said Letters Patent is hereby corrected as shown below:

Column 9,
Line 4, please change "clam" to -- claim --.

Column 10,
Line 19, please change "regions wherein" to -- regions, wherein --.

Signed and Sealed this

Eleventh Day of October, 2005

JON W. DUDAS
*Director of the United States Patent and Trademark Office*